United States Patent
Desai et al.

(10) Patent No.: US 9,539,614 B2
(45) Date of Patent: *Jan. 10, 2017

(54) SURFACE MODIFICATION TO IMPROVE LUBRICITY, ABRASION RESISTANCE AND TEMPERATURE RESILIENCE OF LEADS

(71) Applicant: Cardiac Pacemakers, Inc., St. Paul, MN (US)

(72) Inventors: Shrojalkumar Desai, Lake Bluff, IL (US); Leslie J. Carion, White Bear Lake, MN (US); Larry L. Hum, Cottage Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 885 days.

This patent is subject to a terminal disclaimer.

(21) Appl. No.: 13/735,530

(22) Filed: Jan. 7, 2013

(65) Prior Publication Data

US 2013/0122185 A1    May 16, 2013

Related U.S. Application Data

(63) Continuation of application No. 12/547,839, filed on Aug. 26, 2009, now Pat. No. 8,372,468.

(Continued)

(51) Int. Cl.
*B05D 5/08*  (2006.01)
*A61L 31/10* (2006.01)
(Continued)

(52) U.S. Cl.
CPC ............... *B05D 5/08* (2013.01); *A61L 31/10* (2013.01); *A61L 31/14* (2013.01); *C08J 3/245* (2013.01);
(Continued)

(58) Field of Classification Search
CPC ...... A61L 31/10; A61L 31/14; A61L 2400/18; B05D 5/08; C08J 3/245; C08J 7/06; C08L 23/0853

See application file for complete search history.

(56) References Cited

U.S. PATENT DOCUMENTS

| 3,460,975 | A | 8/1969 | Stebleton |
| 4,851,009 | A | 7/1989 | Pinchuk |

(Continued)

FOREIGN PATENT DOCUMENTS

| EP | 0651005 B1 | 5/1995 |
| EP | 1462129 A1 | 9/2004 |

OTHER PUBLICATIONS

International Search Report and Written Opinion issued in PCT/US2009/055022, dated Nov. 17, 2009, 13 pages.

*Primary Examiner* — Mathieu Vargot
(74) *Attorney, Agent, or Firm* — Faegre Baker Daniels LLP

(57) ABSTRACT

A medical electrical lead body having an outer surface and including at least one lumen having an inner surface treated with a silane surface modifying agent to form a three-dimensional, densely cross-linked lubricious coating over at least a portion of the inner surface of the lumen. The outer surface of the lead body also may be similarly treated. The lubricious silane coating may reduce the coefficient of friction of the coated surface of the lead body by as much as 80% when compared to an uncoated surface. A reduction in the coefficient of friction may enhance the stringing efficiency of a conductor through the lead body lumen and may enhance its abrasion resistance.

15 Claims, 13 Drawing Sheets

Related U.S. Application Data

(60) Provisional application No. 61/098,450, filed on Sep. 19, 2008.

(51) Int. Cl.
*A61L 31/14* (2006.01)
*C08J 3/24* (2006.01)
*C08J 7/06* (2006.01)
*C08L 23/08* (2006.01)

(52) U.S. Cl.
CPC .............. *C08J 7/06* (2013.01); *C08L 23/0853* (2013.01); *A61L 2400/18* (2013.01)

(56) References Cited

U.S. PATENT DOCUMENTS

| | | |
|---|---|---|
| 5,464,650 A | 11/1995 | Berg et al. |
| 5,736,251 A | 4/1998 | Pinchuk |
| 6,060,123 A | 5/2000 | Ogawa |
| 6,329,488 B1 | 12/2001 | Terry et al. |
| 6,463,334 B1 | 10/2002 | Flynn et al. |
| 6,967,040 B2 | 11/2005 | Sato |
| 7,029,755 B2 | 4/2006 | Terry et al. |
| 7,174,221 B1 | 2/2007 | Chen et al. |
| 7,182,906 B2 | 2/2007 | Chen |
| 7,247,364 B2 | 7/2007 | Hossainy et al. |
| 7,365,134 B2 | 4/2008 | Benz et al. |
| 8,372,468 B2 | 2/2013 | Desai et al. |
| 2007/0014828 A1 | 1/2007 | Fitzhugh et al. |
| 2007/0225746 A1* | 9/2007 | Lee et al. .............. A61L 29/085 606/194 |
| 2010/0075018 A1 | 3/2010 | Desai et al. |

* cited by examiner

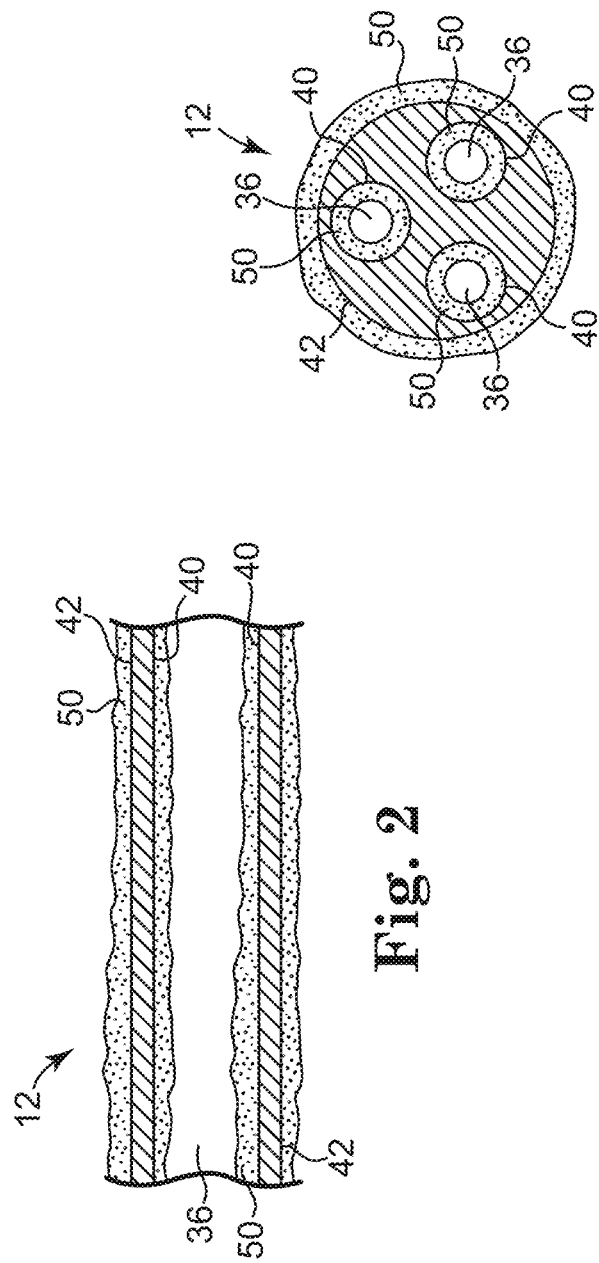

SURFACE MODIFICATION TO IMPROVE LUBRICITY, ABRASION RESISTANCE AND TEMPERATURE RESILIENCE OF LEADS

CROSS REFERENCE TO RELATED APPLICATION

This application is a continuation of U.S. application Ser. No. 12/547,839, filed Aug. 26, 2009, now U.S. Pat. No. 8,372,468, which is a non-provisional application of provisional application Ser. No. 61/098,450, filed on Sep. 19, 2008, which are hereby incorporated herein by reference in their entirety for all purposes.

TECHNICAL FIELD

The present invention relates to a method of treating a surface of an object with a lubricious surface coating. More particularly, the present invention relates to a method of treating a medical electrical lead to reduce the coefficient of friction on the surface of the lead.

BACKGROUND

Silicone rubber is a biostable, thermoset polymer and is commonly used as an insulator in lead body construction. Silicone rubber and other polymers may be subject to abrasion over their lifetime. Another challenge associated with silicone rubber is lead stringing during manufacture of the lead body. Lead stringing refers to pulling a conductor through a lumen provided in the lead body. The tacky surface characteristics of the silicone rubber can hinder the automation of the lead stringing process, making it time consuming and costly.

SUMMARY

According to one embodiment, the present invention is a method for forming a lubricious coating on a lead body including an outer surface and at least one lumen having an inner surface. The method includes contacting the inner and outer surfaces of the lead body with a coating composition comprising a silane surface modifying agent, exposing the surfaces of the lead body to a humid environment, and thereafter curing the coating composition onto at least one of the surfaces to form a siloxane coating.

According to another embodiment, the present invention is a method for forming a lubricious coating on a lead body including an at least one lumen having an inner surface. The method includes contacting the inner surface with a coating composition including a silane surface modifying agent, contacting the inner surfaces with steam, and curing the coating composition on the inner surface of the lead body to form a siloxane coating.

According to another embodiment, the present invention is a coated medical electrical lead made according to the various embodiments as described above.

According to yet another embodiment, the present invention is a medical electrical lead including a lead body having an outer surface and including a first end and a second end and at least one lumen having an inner surface extending there between. The medical electrical lead includes at least one conductor extending through the at least one lumen and at least one electrode operatively coupled to the at least one conductor. A siloxane coating is provided over at least a portion of the inner surface of the at least one lumen. In further embodiments, a siloxane coating is provided over at least a portion of the outer surface of the medical electrical lead.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2 is side cross-sectional view of a portion of a lead body according to an embodiment of the present invention.

FIG. 3 is an end, cross-sectional view of a lead body according to an embodiment of the present invention.

Figure 1:
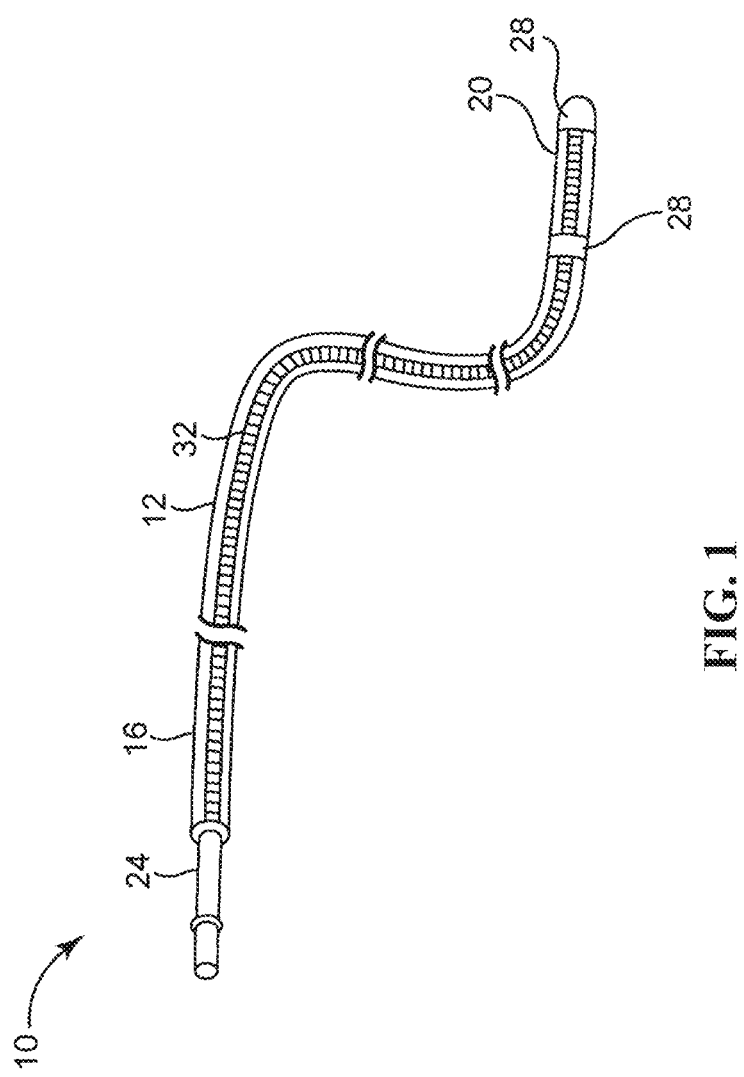
FIG. 1 is a schematic view of a medical electrical lead according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

FIG. 1 is a partial cross-sectional view of a medical electrical lead 10, according to various embodiments of the present invention. According to some embodiments, the medical electrical lead 10 can be configured for implantation within a patient's heart. According to other embodiments, the medical electrical lead 10 is configured for implantation within a patient's neurovascular regions. The medical electrical lead 10 includes an elongated, insulative lead body 12 extending from a proximal end 16 to a distal end 20. The proximal end 16 is configured to be operatively connected to a pulse generator via a connector 24. At least one conductor 32 extends from the connector 24 at the proximal end 16 of the lead 10 to one or more electrodes 28 at the distal end 20 of the lead 10. The conductor 32 can be a coiled or cable conductor. According to some embodiments where multiple conductors are employed, the lead can include a combination of coiled and cable conductors. When a coiled conductor is employed, according to some embodiments, the conductor can have either a co-radial or a co-axial configuration.

The lead body 12 is flexible, but substantially non-compressible along its length, and has a circular cross-section. According to one embodiment of the present invention, an outer diameter of the lead body 12 ranges from about 2 to about 15 French. The medical electrical lead 10 may be unipolar, bipolar, or multi-polar depending upon the type of therapy to be delivered. In embodiments of the present invention employing multiple electrodes 28 and multiple conductors 32, each conductor 32 is adapted to be connected to an individual electrode 28 in a one-to-one manner allowing each electrode 28 to be individually addressable.

Additionally, the lead body 12 can include one or more lumens. In some embodiments at least one lumen is adapted to receive the insertion of a conductor during construction of the medical electrical lead. In further embodiments, at least one lumen is adapted to receive a guiding element such as a guidewire or a stylet for delivery of the lead 10 to a target location within a patient's heart.

The electrodes 28 can have any electrode configuration as is known in the art. According to one embodiment of the present invention, at least one electrode can be a ring or partial ring electrode. According to another embodiment, at least one electrode 52 is a shocking coil. According to yet another embodiment of the present invention, at least one electrode 28 includes an exposed electrode portion and an insulated electrode portion. In some embodiments, a combination of electrode configurations may be used. The electrodes 28 can be coated with or formed from platinum, stainless steel, MP35N, a platinum-iridium alloy, or another similar conductive material. In further embodiments, a steroid eluting collar may be located adjacent to at least one electrode 28.

According to various embodiments, the lead body 12 can include one or more fixation members for securing and stabilizing the lead body 12 including the one or more electrodes 28 at a target site within a patient's body. The fixation member(s) can be active or passive. In some embodiments, the fixation member can be a screw-in fixation member. In other embodiments, the fixation member can be an extendable/retractable fixation member and can include one or more mechanical components adapted to facilitate the extension/retraction of the fixation member. An exemplary extendable/retractable fixation member is shown and described in U.S. Pat. No. 6,463,334 which is herein incorporated by reference.

FIG. 2 is a cross-sectional view of a portion of a lead body 12, according to various embodiments of the present invention. FIG. 3 is an end cross-sectional view of a lead body 12 according to other embodiments of the present invention. The lead body 12, as shown in FIG. 2, includes at least one lumen 36 having an inner surface 40. In some embodiments, as shown in FIG. 3, the lead body 12 may include two or more lumens 36. According to various embodiments, a lubricious coating 50 is provided over at least a portion of the inner surface 40 of at least one lumen 36. In other embodiments, the lubricious coating can be provided over the inner surfaces 40 of multiple lumens 36. In some embodiments, the lubricious coating 50 is provided over the inner surface 40 of at least one lumen 36 such that the coating 50 extends from substantially the proximal end 16 to the distal end 20 of the lead body 12. The lubricious coating 50 provided over the inner surface 40 of at least one lumen 36 may facilitate stringing of a conductor through the lumen 36 during the lead manufacturing process.

According to some embodiments, the lead body 12 can include a lubricious coating 50 disposed over at least a portion of the outer surface 42 of the lead body 12. According to some embodiments of the present invention, the lubricious coating 50 is provided over the outer surface of the insulative lead body such that the coating 50 extends from substantially the proximal end to the distal end of the lead body 12. According to other embodiments of the present invention, the coating 50 is provided at one or more discrete locations along the lead body 12.

According to various embodiments of the present invention, the lead body 12 may include a lubricious coating 50 provided over at least a portion of both the inner and outer surfaces 40 and 42 of the lead body 12. According to other embodiments, the lead body 42 may include a lubricious coating 50 provided over only at least a portion of an inner surface 40 of at least one lead body lumen 36. According to yet other embodiments, the lead body 12 may include a lubricous coating provided over at least a portion of the outer surface 42 of the lead body 12.

According to further embodiments of the present invention the coating 50 may be provided over the surfaces of other suitable substrates. Exemplary suitable substrates include, but are not limited to, the following: o-rings, seals, fixation mechanisms (including an extendable/retractable fixation mechanism and its mechanical components), pulse generator housing, stents, or any other substrate having a surface where a lubricious coating or a reduction in the coefficient of friction is desired.

According to various embodiments of the present invention, the lubricious silane coating 50 is formed by cross-linking a coating composition including a silane surface modifying agent onto the inner 40 and/or outer surface 42 of the lead body 12 or other suitable substrate. Exemplary silane surface modifying agents are described in U.S. Pat. No. 5,736,251, which is incorporated by reference herein in its entirety. According to one embodiment, the coating composition includes a silane surface modifying agent having the following general formula:

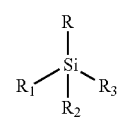

Formula I wherein: R is selected from unsubstituted and halogen-substituted aliphatic, cycloaliphatic, aromatic and linear and branched alkyl-substituted aromatic groups having less than or equal to about fifteen carbons or wherein R is selected from oligomers and other short chain polymers where the number of monomer units ranges from 1 to 15; and $R_1$, $R_2$, and $R_3$ are each independently selected from hydrogen, hydroxy, halogen, alkyl, halogen-substituted alkyl, acyl, acetoxy, alkoxy, and acyloxy groups, and combinations thereof.

According to some embodiments, the functional groups $R_1$, $R_2$, and $R_3$ silane may be the same for maximum cross-link density and functionality. The functional groups selected for either $R_1$, $R_2$, and/or $R_3$ may be any good silane leaving group which can be independently selected from hydrogen, halogen, hydroxyl, alkoxy, and acyloxy groups. According to some exemplary embodiments, good leaving groups for use as any or all of the $R_1$, $R_2$, or $R_3$ substituents include methoxy, ethoxy, acetoxy, and the like, as well as mixtures thereof, or hydroxy or chloro groups. According to other embodiments, in which lower cross-linked functionality may be tolerated the functional groups selected for $R_2$ and $R_3$ substituents may be different from either $R_1$ or each other.

According to some embodiments, the silane moiety or R group can be selected from aliphatic, cycloaliphatic, aromatic and alkyl aromatic groups having less than or equal to 15 carbon atoms. The R groups may be unsubstituted or may be substituted with halogen groups such as chloro, bromo or fluoro groups or may be mixtures of any of the foregoing. Exemplary silane moieties for use as the R group of the above formula are lower $C_1$-$C_8$ alkyl groups such as methyl, ethyl, propyl, and butyl and the like, as well as, halo-substituted alkyls, such as 1,1,1-trifluoropropyl, or an aromatic group, such as benzyl or tolyl groups. According to yet other embodiments of the invention, the R group may be polyethylene glycol (PEG) or polyvinyl pyrrolidone (PVP).

Exemplary silane surface modifying agents according to Formula 1 and for use with various embodiments of the present invention include, but are not limited to, the following: methyltriacetoxysilane, ethyltriacetoxysilane, propyltriacetoxysilane, methyltrichlorosilane, ethyltrichlorosilane, 1,1,1-trifluoropropyl-methyldimethoxysilane, trifluoroethyl trichlorosilane, and trifluoroethyl trifluorosilane. The silanes in accordance with Formula I are generally available commercially from several sources including Hüls America, Inc., Piscataway, N.J. Synthetic methods for making the silane monomers or coating precursors defined by the formula are generally well known to those skilled in this art.

According to other embodiments of the present invention, mixtures of any of the silane surface modifying agents defined by Formula I may be used to provide a lubricious silane coating on the inner and/or outer surfaces of a lead body or other suitable substrate. According to still other embodiments, mixtures of silane surface modifying agents having varying functionality may also be used to provide a lubricous coating on the inner and/or outer surfaces of a lead body or other suitable substrate.

According to various embodiments of the present invention, the silane surface modifying agents can be used to coat a surface of a variety of substrates having surface groups present on the surface of the substrate capable of reacting with the silane surface modifying agents. The silane surface modifying agents react with the reactive groups present on the surface of the substrate to form a three-dimensional, cross-linked, lubricious silane coating. According to some embodiments, the substrate to be coated includes a plurality of hydroxyl (OH) groups or other activated hydrogen (H) groups present on the surface of the substrate. According to various embodiments, the substrate to be coated may include any polymeric, copolymeric, natural or synthetic elastomeric material including surface groups reactive with the silanes to form the three dimensional cross-linked coating matrix. Exemplary substrate materials having either active OH groups and/or active H groups present on the surface include, but are not limited to, the following: polyamides, polyesters, polyurethanes, silicones, acetoxy-derived silicones, silanol-terminated silicones, polysiloxanes, polyurethanes, nylon, polyolefin polymers, rubbery copolymers, butyl rubbers, butyl nitrile rubbers, polyisoprenes, isobutylene copolymers, siloxane-urethane copolymers, and the like. According to other embodiments, the silane surface modifying agents may also be used to coat the surfaces of metal or other materials as desired.

According to some embodiments of the present invention, a silane surface modifying agent according to Formula I can also be used to provide a lubricious coating on a substrate having an inert surface. The inert surface is first pre-treated to provide groups capable of reacting with the silanes on the surface of the substrate. Pre-treatment of the substrate surface may increase adhesion of the lubricious coating to the substrate. Exemplary chemical surface treatments include chemical etching, surfactant adsorption, co-extrusion, actinic radiation, such as plasma discharge, surface oxidation or reduction, and surface grafting with materials such as polyvinyl alcohol, poly(2-hydroxyethyl methacrylate) and the like. Bulk modifications of the substrate surface can also be accomplished in order to provide active hydrogens. Examples of conventional modifications of this type include: blending with polymers having active hydrogens; partial degradation of polymers; end group modification; monomer functionalization; oxidation; reduction; copolymerization; and the like. According to one embodiment, surface oxidation of the substrate surface may be used to pre-treat the surface. Additionally, the substrate to be coated may undergo auto-oxidation or be subject to environmental oxidation resulting in the formation of reactive surface groups. Reactive surface groups may also be provided via the method used to manufacture the substrate. For example, reactive surface groups may be formed on the surface of the substrate to be coated during an extrusion process.

Figure 4:
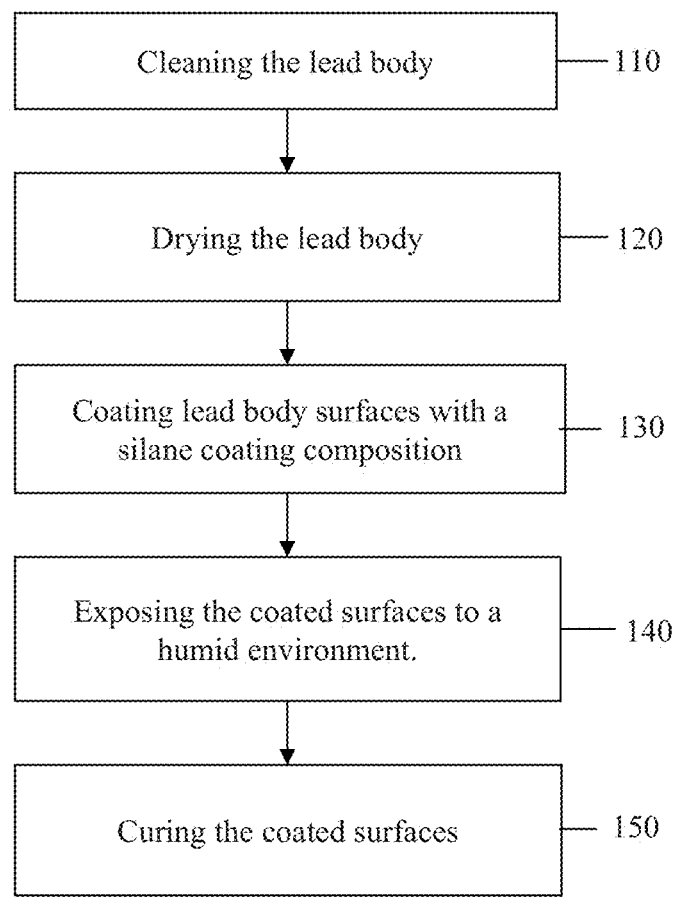
FIG. 4 is a flow chart of a method according to an embodiment of the present invention.

FIG. 4 is a flow chart of a method 100 used to form a three-dimensional lubricious silane coating on an inner and/or an outer surface 40 and/or 42 of a lead body 12 or other suitable substrate having a surface to be coated. Prior to coating the inner and/or outer surfaces 40 and/or 42 of the lead body 12, the lead body 12 or other substrate is cleaned and rinsed using a variety of cleaning methods known to those of skill in the art (Block 110). For example, the lead body 12 or substrate is sonicated or immersed in a solvent and then rinsed with copious amounts of fresh solvent. Suitable solvents useful for cleaning and rinsing the lead body 12 or substrate are well known to those of skill in the art.

After cleaning, the lead body 12 is dried at room temperature, in an oven or a combination thereof (Block 120). According to some embodiments, the lead body 12 or substrate is dried for a period of time of less than about 1 hour. For example, the substrate may be dried for a period of time ranging from about 5 to about 60 minutes, about 10 to about 55 minutes, about 15 to about 50 minutes, about 20 to about 45 minutes, about 25 to about 40 minutes, about 30 to about 35 minutes, or about 15 to about 25 minutes. According to another embodiment, the lead body 12 or substrate is dried at a temperature of less than about 155° C. For example, the lead body 12 or substrate is dried at a temperature ranging from about 50° to about 110° C., more particularly about 60° to about 80° C.

According to one embodiment, the lead body or substrate is dried in an environment having a relative humidity of greater than about 5%. For example, the initial drying step can take place in an environment having a relative humidity ranging from about 35% to about 95%. The lead body 12 or substrate may then be further air-dried and cooled at room temperature.

Desired surfaces of the lead body 12 are then coated with a composition containing the silane modifying agent (Block 130). According to one embodiment, the lead body 12 or other suitable substrate can be coated by dip-coating or immersing the lead body 12 or substrate in a coating composition including one or more silane surface modifying agents according to Formula I and a solvent. Other coating methods known to those of skill in the art such as spray-coating or vapor deposition may also be employed.

In one embodiment, the coating comprises at least about 2% percent by weight of silane modifying agent, more particularly between about 2 and about 10 percent by weight silane modifying agent. The coating composition may also include one or more solvents. Suitable solvents include any organic solvent in which the silanes of the formula are soluble or at least partially soluble at room temperature. Illustrative examples include hydrocarbon solvents and halo-hydrocarbon solvents. According to some embodiments, the selected solvents are non-polar and non-aromatic organic solvents. Other illustrative solvents which may be used to form the coating composition include: pentane, cyclohexane, heptane, xylene, short chain halohydrocarbons and silicone fluids, such as poly dimethylsiloxane oils, for example, Dow Corning Medical Fluid 200 and the like.

According to some embodiments, the coating compositions may optionally include a cross-linking catalyst in an amount effective to promote more complete or more rapid curing of the coatings at a given desired cure temperature range. Generally, known siloxane catalysts familiar to those skilled in the art may be used including organo-metallic catalysts based on lead, tin, zinc and titanium compounds, as well as, quaternary compound catalysts. The catalysts may be used in amounts ranging from 0.0001% to about 5.0% by weight, based upon the total weight of silane component(s). Especially preferred catalysts include dialkylmetal mono- or polycarboxylates, such as stannous octoate, dibutyltin dilaurate and dibutyltin diacetate.

The lead body 12 or substrate is dip-coated in, or otherwise contacted with, the coating composition for a sufficient amount of time such that all surfaces of the lead body 12 or substrate to be coated, including any inner surfaces 40, are contacted with the coating composition. According to one embodiment, the lead body 12 or substrate is immersed in the coating composition for a minimum of two minutes. For example, the lead body 12 or substrate may be immersed in the coating composition for about 2 to about 20 minutes, about 5 to about 15 minutes, about 7 to about 12 minutes, or about 10 minutes.

The coating thickness is affected by the immersion time. Generally, the longer the lead body 12 or substrate is immersed in the coating composition, the thicker the coating. According to one embodiment, the coating thickness ranges from about 0.01 microns to about 200 microns. According to another embodiment, the coating thickness ranges from about 5 microns to about 25 microns. According to various embodiments, the coating thickness is generally greater than the thickness of any priming agents or coupling agents that may be applied in one or multiple layers to pre-treat the surfaces of the lead body 12 or substrate to be coated.

The coated surfaces of the lead body 12 are then exposed to a humid environment (Block 140). According one embodiment of the present invention, the lead body 12, or at least the coated portions thereof, are placed in a humidity chamber or similar humid environment. The humid environment can be result of water vapor, condensation, or other build-up of moisture in the environment. For example, the lead body 12 can be placed in a chamber having a humidity level of between about 5 and about 85 percent, more particularly between about 50 and about 85 percent, and even more particularly between about 65 and about 75 percent. The lead body can be placed in the humidity chamber for between about 30 seconds and about 10 minutes, more particularly between about 1 and about 5 minutes. As demonstrated in the examples, a more complete and/or uniform coating of the outer surface of the lead body may be achieved by exposing the outer surface to high humidity.

According to another embodiment, one or more lumens 36 of the lead body 12 are exposed to a high humidity environment by contacting the lumens with steam. According to one embodiment, steam is injected into the lumen(s) 36 for a minimum of 5 seconds. In another embodiment, steam is injected for a period of time ranging from about 5 seconds to about 300 seconds (5 minutes). In still another embodiment, steam is injected for a period of time ranging from about 15 seconds to about 1 minute. As demonstrated in the examples, a more complete and/or uniform coating in the inner lumen may be achieved by steam injection. In a further embodiment, the steam can be superheated steam. Superheated steam is steam at a temperature higher than its boiling point at a given pressure According to certain embodiments, the lead body 12 may first be placed in a humidity chamber and then the inner lumen(s) 36 may be contacted with steam, or vice versa, to provide coatings on the outer surface and inner lumen. According to other embodiments, both steps could occur simultaneously with the steam injection acting as the humidity source in a closed vessel.

According to another embodiment, the process of coating the inner and outer surfaces 40, 42 of the lead body 12 or substrate can be combined into a single step. For example, after the lead body 12 or substrate has been contacted with the coating composition, both the inner surface 40 and outer surface 42 of the lead body 12 or substrate can be contacted with steam. The inner surface 40 and outer surface 42 can be contacted with steam by blasting steam through the lumen 36 of the lead body 12 while at the same time, blasting steam over the outer surface 42 of the lead body 12. The steam contacting step is performed for a sufficient amount of time such that all available reactive sites on the inner and outer surfaces 40, 42 of the lead body 12 or substrate are exposed to humidity. For example, steam can be blasted into the lumen 36 and onto the outer surface 42 of the lead body 12 for a period of time ranging from about 5 seconds to about 5 minutes or, more particularly, for a period of time ranging from about 15 seconds to about 1 minute. The coating is then cured on the inner surface 40 and the outer surface 42 of the lead body 12 following the method as described above.

After exposure to the humid environment, the lead body 12 is then placed in an oven under controlled temperature and humidity conditions to cure the coating on the inner surface 40 of the lead body 12 or substrate (Block 150). According to some embodiments, the coating on the inner surface 40 of the lead body 12 or substrate is cured for a period of time ranging from about 5 minutes to about 2 hours, more particularly, from about 30 to about 90 minutes, even more particularly from about 45 to about 75 minutes. The lead body 12 may be cured at a temperature of ranging from about 65° C. to about 155° C., even more particularly from about 100° C. to about 120° C. According to one embodiment, the coating on the inner surface 40 of the lead body 12 or substrate is cured in an environment having a relative humidity of greater than about 5%. For example, the curing step takes place in an environment having a relative humidity ranging from about 35% to about 95%. The lead body 12 is then removed from the oven and allowed to further air-dry and cool to room temperature. According to another embodiment, the coating is cured in an oven in which no additional humidity is introduced.

After curing is complete, the coated surfaces can be rinsed repeatedly in water or organic solvents without substantially modifying the three-dimensional matrix formed on the surfaces. Rinsing of the coated surfaces may be carried out repeatedly in order to remove any as yet unreacted or unbound silane or polymer residue within the matrix.

As further exhibited in the Examples set forth below, the silane surface modifying agent, reacts with surface reactive groups on the surface of the suitable substrate to provide a densely cross-linked silane coating which is chemically bonded to the surface. The resulting coating forms a three-dimensional matrix on the surface of the substrate as well as a cross-linked interpenetrating network within the substrate. The three-dimensional coating may reduce the coefficient of friction of the surface compared to an uncoated surface. A reduction in the surface coefficient for the coated substrate may increase its lubricity and/or its abrasion resistance.

The coatings of certain embodiments, in particular those utilizing ethyltriacetoxysilane in the coating, have the appearance of very small droplets on the surface of the substrate. These hemispherical, micro-nodular coating matrix formations may further reduce the surface coefficient of friction for the coated substrate. Curing reactions performed in less humid environments and/or without pre-humidification or moisturization of the substrate to be modified or coated still provide very useful lubricious coatings which effectively reduce surface friction characteristics and tackiness. Additionally, the lubricious coating formed on the inner and/or outer surfaces of a lead body according to the various embodiments of the present invention does not substantially increase the inner diameter and/or outer diameter of the lead body. According to one embodiment, the increase in the inner and/or or outer diameter of the lead body is less than about 0.002 inch.

According to various embodiments of the present invention, According to one embodiment, a lubricious silane coating provided on a surface of a substrate according to the embodiments described above, reduces the coefficient of friction of the surface by as much as 80% when compared to an uncoated surface as will be demonstrated by the examples to follow.

Example 1

Samples of silicone tubing were sonicated for 1 hour in 500 mL of heptane and then rinsed with clean heptane. Each end of the tubing samples was wicked with a Kimwipe® and the samples were placed in an oven at 70° C. with equal to or less than room humidity for 2 hours.

Figure 5A:
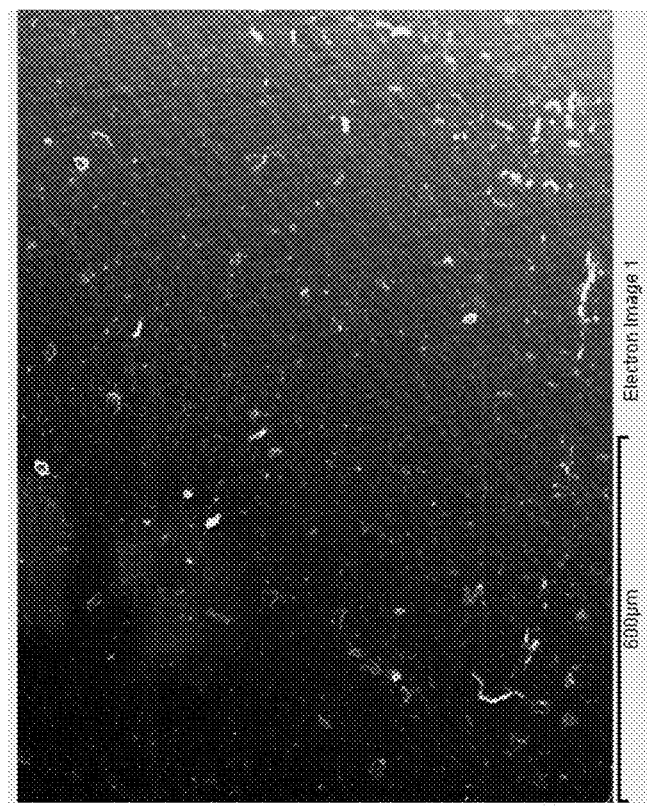
FIGS. 5A-5B are scanning electron microscope images of a tubing sample as described in Example 1.
Figure 5B:
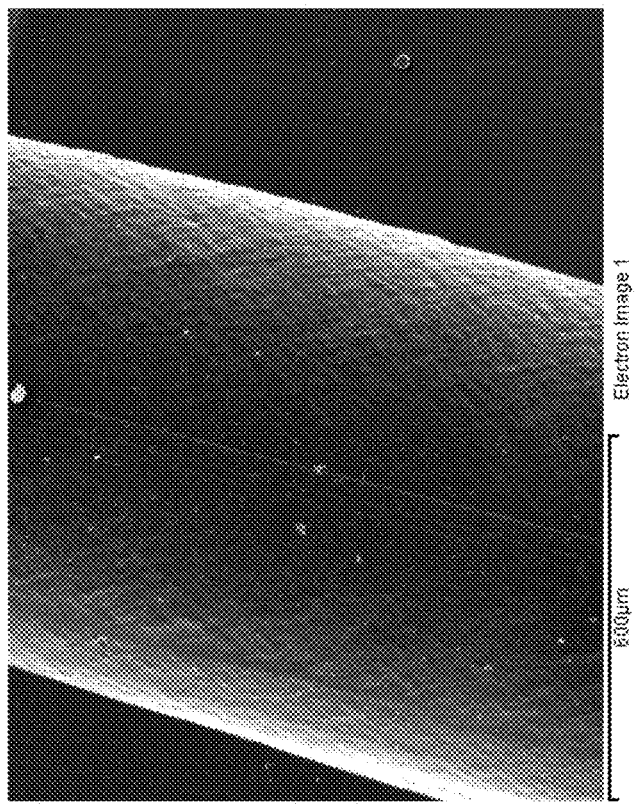

The tubing samples were removed from the oven and dipped for 15 minutes in a solution containing 5.5 wt % ethyltriacetoxysilane (ETA) in 60 mL heptane. The tubing samples were removed from the ETA solution and each end of the tubing samples was wicked with a Kimwipe®. The samples were then cured at 110° C. in an oven, into which no additional humidity was introduced, for one hour. FIGS. 5A and 5B are SEM photos of the inner surface of the lumen and outer surface of one of the samples after curing. As shown in FIGS. 5A and 5B, the outer surface and inner lumen surface of the samples were not substantially coated with ETA.

Example 2

Samples of silicone tubing were sonicated for 1 hour in 500 mL of Heptane and then rinsed with clean heptane. The samples were dried at room temperature for 25 minutes. Each end of the tubing samples was wicked with a Kimwipe® and the samples were placed in an oven at 70° C. with equal to or less than room humidity for 15 minutes.

Figure 6A:
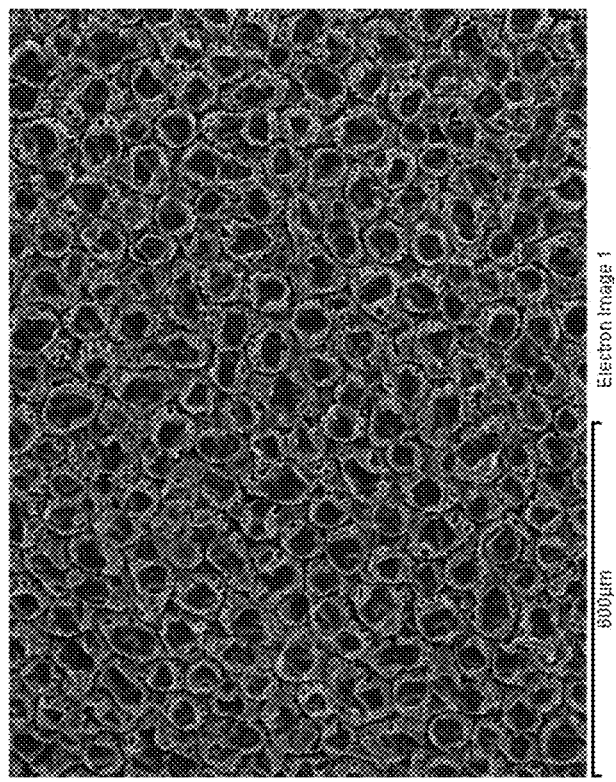
FIGS. 6A and 6B are scanning electron microscope images of an outer surface and an inner surface of a lumen of a tubing sample as described in Example 2.
Figure 6B:
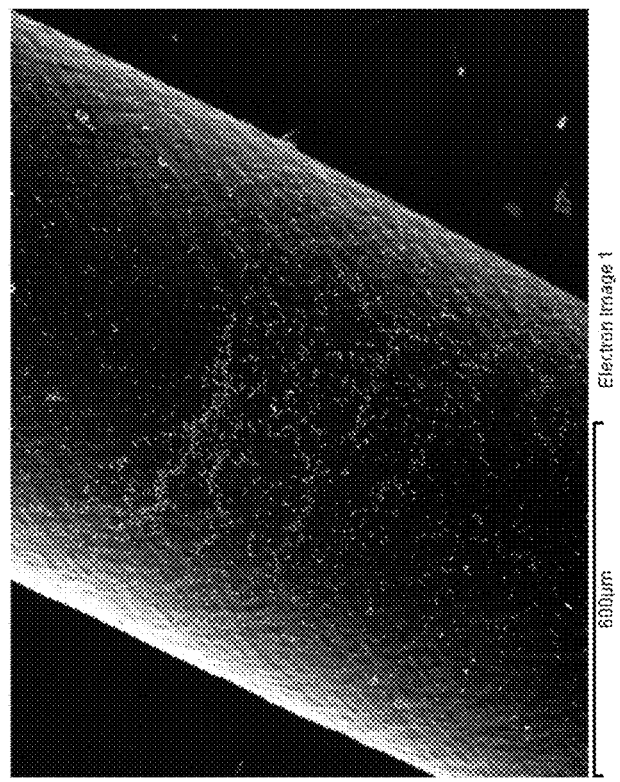

The tubing samples were removed from the oven and dipped for 10 minutes in a solution containing 5.5 wt % ethyltrichlorosilane (ETC) in 60 mL heptane. The tubing samples were removed from the ETC solution and placed in a 70% humidity chamber for 1 minute. The samples were then cured at 110° C. in an oven, into which no additional humidity was introduced, for one hour. FIGS. 6A and 6B are SEM photos showing the outer surface and inner lumen of one of the samples. As shown in FIGS. 6A and 6B a complete, generally uniform coating was formed on the outer surface of the tubing sample, however, a non-uniform coating was formed on the inner lumen as evidenced by the white speckled artifacts in FIG. 6B.

Example 3

Figure 7:
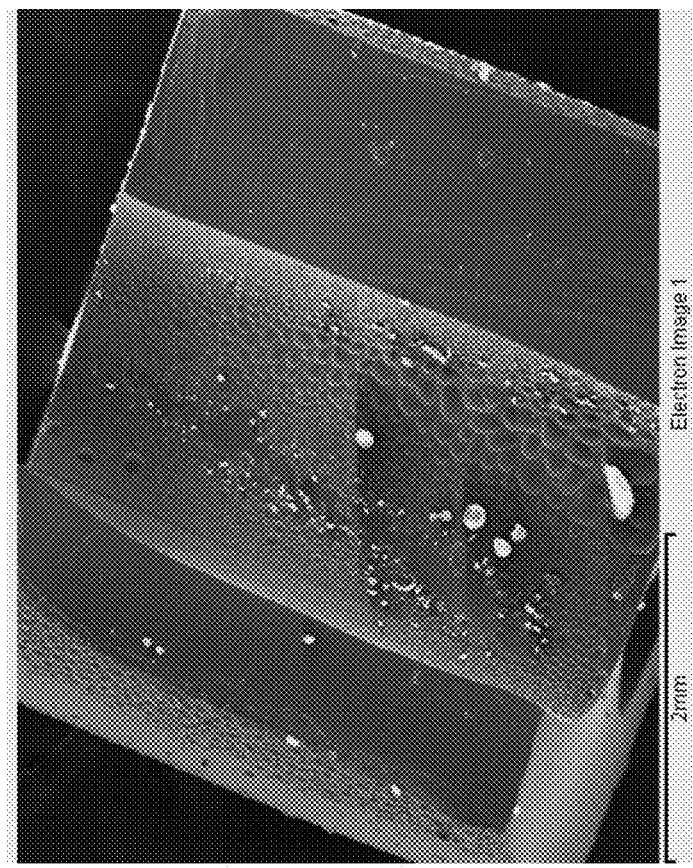
FIG. 7 is a scanning electron microscope images of an inner surface of a lumen of a tubing sample provided with a coating as described in Example 3.

The experiment set forth in Example 2 was repeated using substantially the same protocol except that tubing samples were coated with an ETA solution instead of an ETC solution. FIG. 7 is an SEM image of the inner lumen of one of the samples, which shows that a non-uniform coating was formed on the inner lumen.

Example 4

Figure 8A:
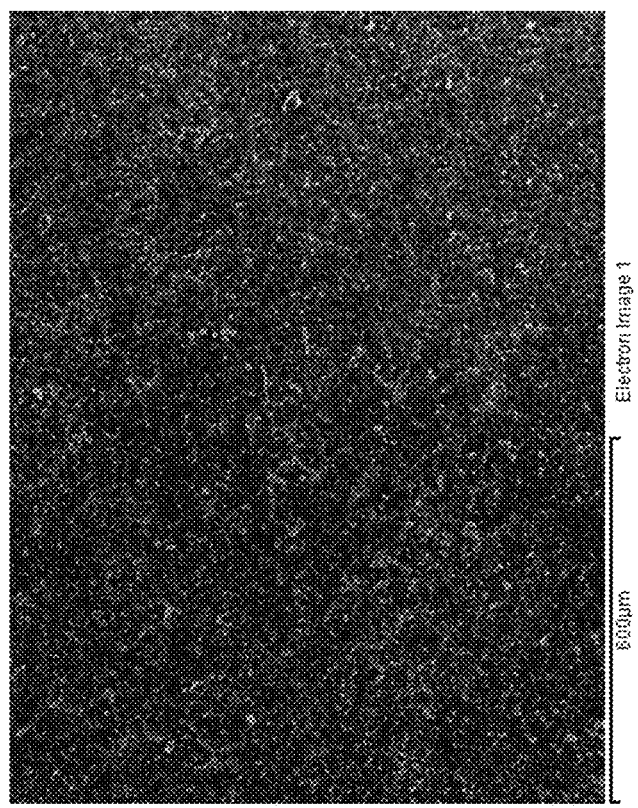
FIGS. 8A and 8B are scanning electron microscope images of an outer surface and an inner surface of a lumen of a tubing sample as described in Example 4.
Figure 8B:
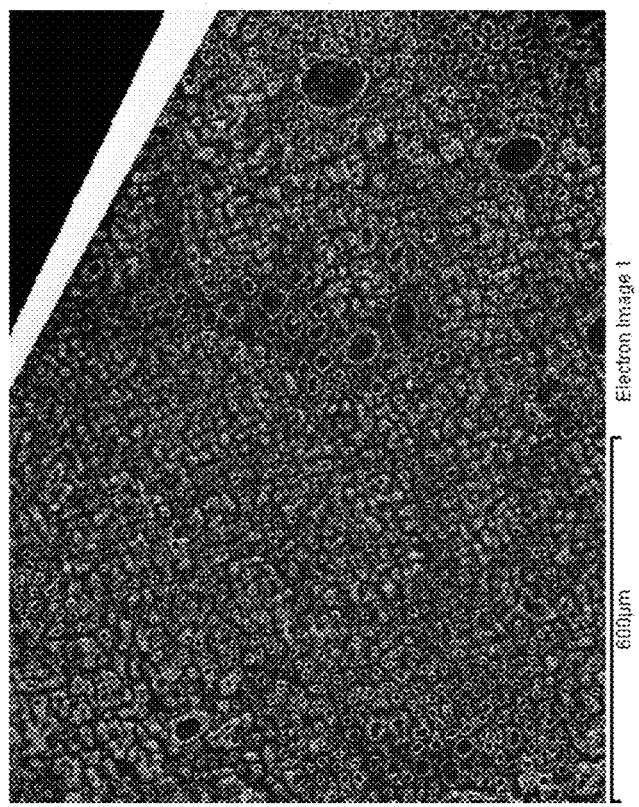

The experiment set forth in Example 2 was repeated using substantially the same protocol except that prior to being placed in the humidity chamber, steam was injected into the inner lumen of the samples for between 30 second and one minute. FIGS. 8A and 8B are SEM images of the outer surface and inner lumen of one of the samples. These figures show that a complete and substantially uniform coating was formed on both the outer surface and inner lumen of the sample.

Example 5

Samples of silicone tubing were sonicated for 1 hour in 500 mL of Heptane and then rinsed with clean heptane. The samples were dried at room temperature for 5 minutes. Each end of the tubing samples was wicked with a Kimwipe® and the samples were placed in an oven at 70° C. with equal to or less than room humidity for 20 minutes. The samples were then air dried for an additional 5 minutes.

Figure 9A:
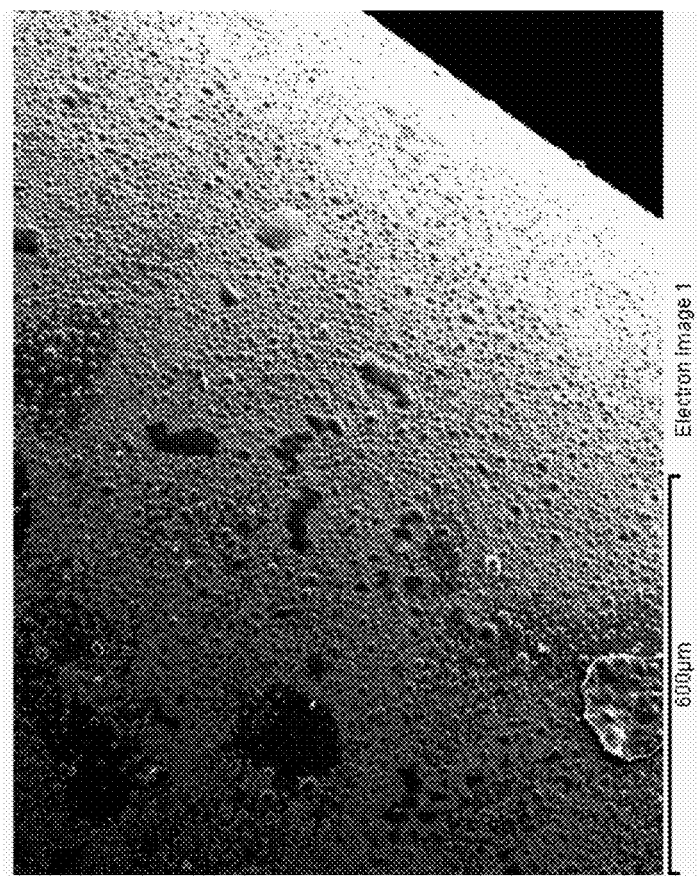
FIGS. 9A-9C are scanning electron microscope images of an outer surface and an inner surface of a lumen of a tubing sample as described in Example 5.
Figure 9B:
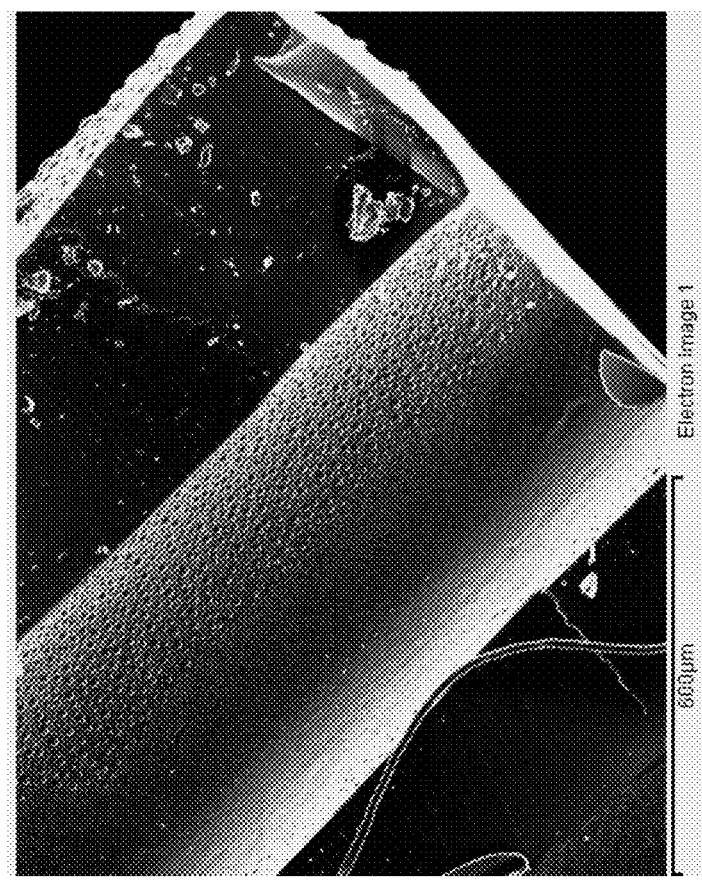
Figure 9C:
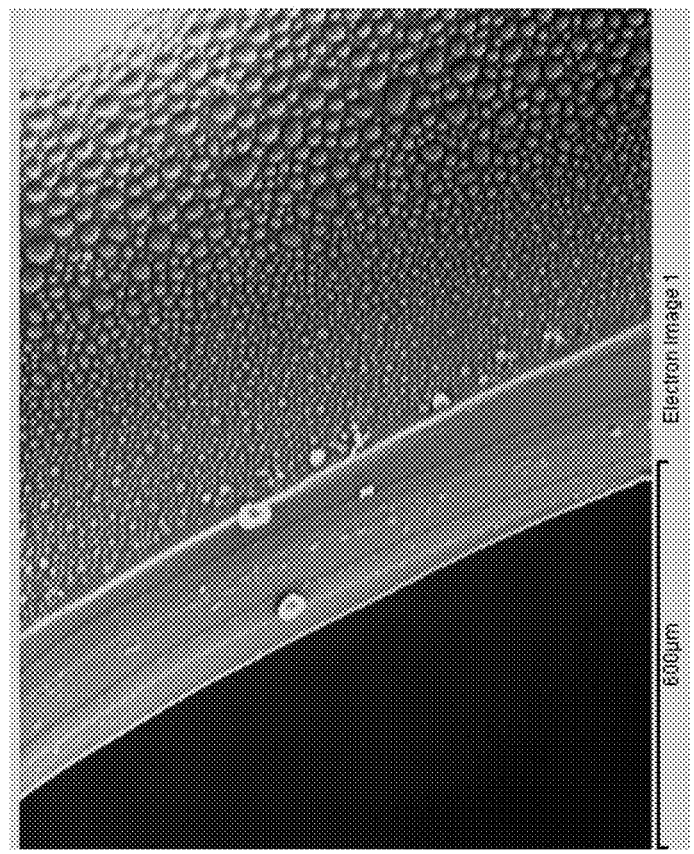

The tubing samples were then dipped for 10 minutes in a solution containing 5.5 wt % ethyltriacetoxysilane (ETA) in 60 mL heptane. The tubing samples were removed from the ETA solution and placed in a 75% humidity chamber for 1 minute and steam was injected into the inner lumen of the samples for between 30 seconds and one minute. The samples were then cured at 110° C. in an oven, into which no additional humidity was introduced, for one hour. FIGS. 9A-9C show the outer surface and inner lumen of one sample. These Figures show a substantially complete coating on both the outer surface and inner lumen. Additionally, at least portions of the coating on both surfaces had a hemispherical morphology.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for forming a lubricious coating on an inner surface of a lumen of a lead body, the method comprising:
   a) contacting the inner surface with a coating composition comprising a solvent and a silane surface modifying agent having a general formula of:

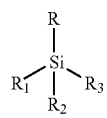

wherein: R is selected from the group consisting of unsubstituted and halogen-substituted aliphatic, cycloaliphatic, aromatic and linear and branched alkyl-substituted aromatic groups having less than or equal to about fifteen carbons or wherein R is selected from the group consisting of short chain polymers where the number of monomer units ranges from 1 to 15; and $R_1$, $R_2$, and $R_3$ are each independently selected from the group consisting of hydrogen, hydroxy, halogen, alkyl, halogen-substituted alkyl, acyl, acetoxy, alkoxy and acyloxy groups, and combinations thereof;
   b) injecting steam into the lumen to contact the inner surface with steam; and
   c) curing the coating composition on the inner surface after the injecting step to form a siloxane coating.

2. The method according to claim 1, wherein the step of contacting the inner surface with the coating composition comprises immersing the lead body in the coating composition.

3. The method according to claim 1, wherein the silane surface modifying agent includes ethyltrichlorosilane.

4. The method according to claim 1, wherein the silane surface modifying agent includes ethyltriacetoxysilane.

5. The method according to claim 1, wherein the silane surface modifying agent is trifluoroethyl trichlorosilane.

6. The method according to claim 1, wherein R is selected from the group consisting of unsubstituted and halogen-substituted aliphatic, cycloaliphatic, aromatic and linear and branched alkyl-substituted aromatic groups having less than or equal to about fifteen carbons.

7. The method according to claim 1, wherein R is polyethylene glycol or polyvinyl pyrrolidone.

8. The method according to claim 1, wherein R is any one of a $C_1$-$C_8$ alkyl group.

9. The method according to claim 1, wherein R is a fluoro-substituted alkyl.

10. The method according to claim 1, wherein the lead body includes an outer surface, and the method further comprises the step of exposing the outer surface to a humid environment prior to the curing step.

11. The method of claim 10, wherein the exposing and injecting steps occur simultaneously.

12. The method according to claim 1, wherein the step of contacting the inner surface with the coating composition comprises immersing the lead body in the coating composition for at least two minutes.

13. The method according to claim 1, wherein the step of curing the coating composition on the inner surface comprises exposing the lead body to an environment having a temperature of about 65 to about 155° C.

14. The method according to claim 1, wherein the silane surface modifying agent is any one of methyltriacetoxysilane, ethyl-triacetoxysilane, propyltriacetoxysilane, methyltrichlorosilane, ethyltrichlorosilane, 1,1,1-trifluoropropylmethyldimethoxysilane, trifluoroethyl trichlorosilane or trifluoroethyl trifluorosilane.

15. The method of claim 10, wherein the exposing step occurs prior to the injecting step.

* * * * *